ized Patent [19]

United States Patent [19]

Stevenson et al.

[11] Patent Number: 4,579,866
[45] Date of Patent: Apr. 1, 1986

[54] PHENYLACETAMIDES AS ANTI-ALLERGY, ANTI-ASTHMA AND ANTI-INFLAMMATORY AGENTS

[75] Inventors: David Stevenson, Scarsdale; Robert C. Liu, White Plains; Laurence L. Ho, New Rochelle; Howard Jones, Ossining; Stephen Coutts, Scarsdale, all of N.Y.

[73] Assignee: USV Pharmaceutical Corp., Tarrytown, N.Y.

[21] Appl. No.: 614,579

[22] Filed: May 29, 1984

[51] Int. Cl.⁴ .................. A61K 31/24; A61K 31/195; C07C 101/04
[52] U.S. Cl. .................. 514/539; 514/563; 560/40; 562/445
[58] Field of Search .................. 560/40, 41; 564/183, 564/185, 170, 174, 176, 182; 514/539, 567, 563; 562/445, 449, 450

[56] References Cited

U.S. PATENT DOCUMENTS 3,586,713 6/1971 Buu-Hoi et al. .................. 564/170

FOREIGN PATENT DOCUMENTS 57-139052 8/1982 Japan .................. 564/182
2083457 3/1982 United Kingdom .

OTHER PUBLICATIONS

Gilbert et al., *Chemical Abstracts*, vol. 85, No. 122759e, (1976).
Obrecht et al., *Chemical Abstracts*, vol. 95, No. 62673s, (1981).
Viel et al., *Chemical Abstracts*, vol. 65, No. 13651h, 1966.
Belsten et al., *Chemical Abstracts*, vol. 60, No. 7992a, 1964.
Kupchan et al., *Chemical Abstracts*, vol. 66, No. 38094j, 1967.
Bottcher et al., *Chemical Abstracts*, vol. 44, No. 8334g, 1950.
Starmer et al., *Chemical Abstracts*, vol. 75, No. 47094x, 1971.

*Primary Examiner*—Natalie Trousof
*Assistant Examiner*—Bruce D. Gray

[57] ABSTRACT

Compounds of the structure

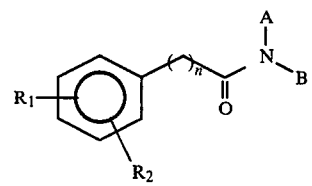

and pharmaceutically acceptable salts thereof, wherein:
$R_1$ and $R_2$ are independently H, OH, lower alkyl, lower alkoxy, aryloxy, heteroaryloxy, heteroaryl lower alkoxy, aryl, heteroaryl, aryl-lower alkyl, aryl-lower alkoxy, halogenated aryl-lower alkoxy, lower alkenyl, lower alkynyl, lower alkenoxy, lower alkynoxy, halogen or trifluoromethyl;
A is H, aryl, lower alkyl, aryl-lower alkyl or heteroaryl; and
B is

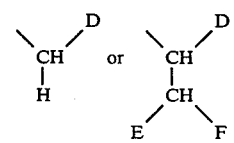

$n = 0-6$,
wherein D is H, $CONR_3R_4$, $CO_2H$, $CO_2R_5$, $CH_2OH$ or $CH_2OR_6$,
wherein
$R_3$, $R_4$, $R_5$ and $R_6$ are independently H, lower alkyl, aryl, aryl-lower alkyl or heteroaryl;
E is H, OH, lower alkyl, aryl or heteroaryl; and
F is

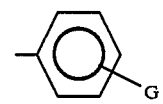

wherein G is the same as $R_1$ and $R_2$,
useful for the treatment of allergy, asthma and inflammatory conditions.

7 Claims, No Drawings

PHENYLACETAMIDES AS ANTI-ALLERGY, ANTI-ASTHMA AND ANTI-INFLAMMATORY AGENTS

DESCRIPTION OF THE INVENTION

Compounds of the structure

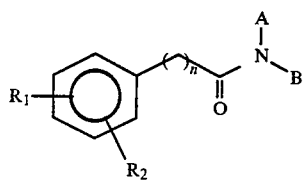

and pharmaceutically acceptable salts thereof, wherein $R_1$ and $R_2$ are independently H, OH, lower alkyl, lower alkoxy, aryloxy, heteroaryloxy, heteroaryl lower alkoxy, aryl, heteroaryl, aryl-lower alkyl, aryl-lower alkoxy, halogenated aryl-lower alkoxy, lower alkenyl, lower alkynyl, lower alkenoxy, lower alkynoxy, halogen or trifluoromethyl;

A is H, aryl, lower alkyl, aryl-lower alkyl or heteroaryl; and

B is

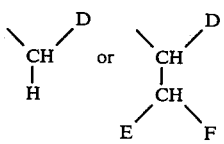

$n = 0-6$,
wherein

D is H, $CONR_3R_4$, $CO_2H$, $CO_2R_5$, $CH_2OH$ or $CH_2OR_6$, wherein $R_3$, $R_4$, $R_5$ and $R_6$ are independently H, lower alkyl, aryl, aryl-lower alkyl or heteroaryl;

E is H, OH, lower alkyl, aryl or heteroaryl; and

F is

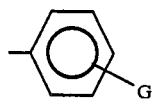

wherein

G is the same as $R_1$ and $R_2$.

The alkyl group and the alkyl moieties in lower alkyl, lower alkoxy, aryl-lower alkyl, aryl-lower alkoxy, lower alkenyl, lower alkynyl, lower alkenoxy and lower alkynoxy contain from 1–6 carbon atoms. The alkyl groups may be branched, unbranched or cyclic.

The aryl group may be phenyl, naphthyl or tolyl.

The heteroaryl group may be tetrazolyl, pyridyl, furanyl, imidazolyl, or indolyl.

Preferred compounds are those in which $R_1$ is lower alkoxy, aryloxy, aryl-lower alkoxy, lower alkenoxy or lower alkynoxy while $R_2$ is aryl, aryl-lower alkyl or halogen, preferably chlorine, and n is 1-2.

Preferred compounds are also the compounds in which:

$R_1$ is halogenated, preferably chlorinated, aryl-lower alkoxy;

$R_2$ is chlorine;

A is H, lower alkyl, or aryl;

B is

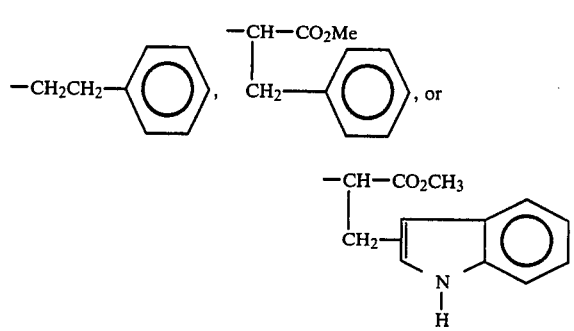

and is 1.

The compounds of this invention may be readily prepared by art-recognized procedures from known starting materials and intermediates can also be prepared from readily available materials using standard organic reactions. Starting materials may also be purchased from chemical supply companies. For example: a, D-phenylalanine, DL-p-chlorophenylalanine ethyl ether hydrochloride, D-tryptophan methyl ester hydrochloride from Sigma; and b, 3-chloro-4-hydroxyphenylacetic acid, 3-chloro-4-hydroxybenzoic acid, L-phenylalaninol, N-benzylethanolamine, 3S-hydroxy-L-phenylalaninol, 1-amino-2-phenylpropane, 1-hydroxy-1-[4-hydroxyphenyl]-2-aminopropane, (+)ephedrine, (−)ephedrine, N-methyl-2-hydroxy-2-phenylethylamine, N-methyl-2-phenylethylamine, 2-hydroxy-2-phenylethylamine, allyl bromide, n-propyl bromide, n-propyl iodide, iso-propyl bromide, benzyl bromide, methyl iodide, cyclopropyl methyl bromide, propargyl bromide from Aldrich.

A schematic procedure for the preparation of compounds of the present invention is as follows:

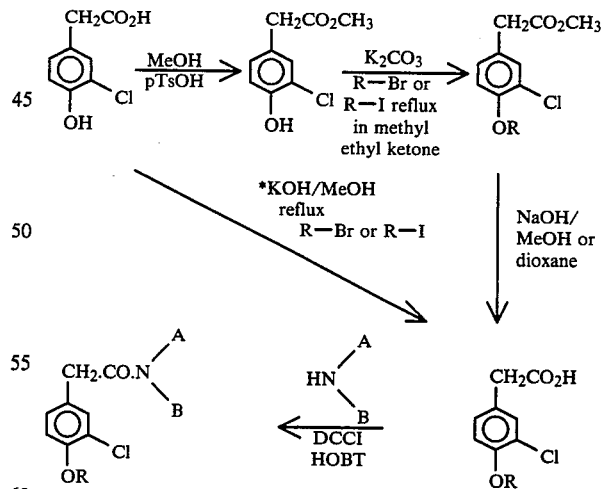

*The 3 step route is preferred; the single step gives relatively low yields.

Compounds of this invention can contain asymmetric centers. Individual optical diastereoisomers as well as mixtures thereof are considered to be within the scope of this invention. When diastereoisomeric products result from the synthetic procedures, the desired diastereoisomeric product can be separated by conventional chromatographic or fractional crystallization methods.

The invention will be more fully illustrated in the examples (1A through 1D) leading to the preparation of 4-benzyloxy-3-chlorophenylacetyl-D-phenylalanine methyl ester. The reaction scheme is as follows:

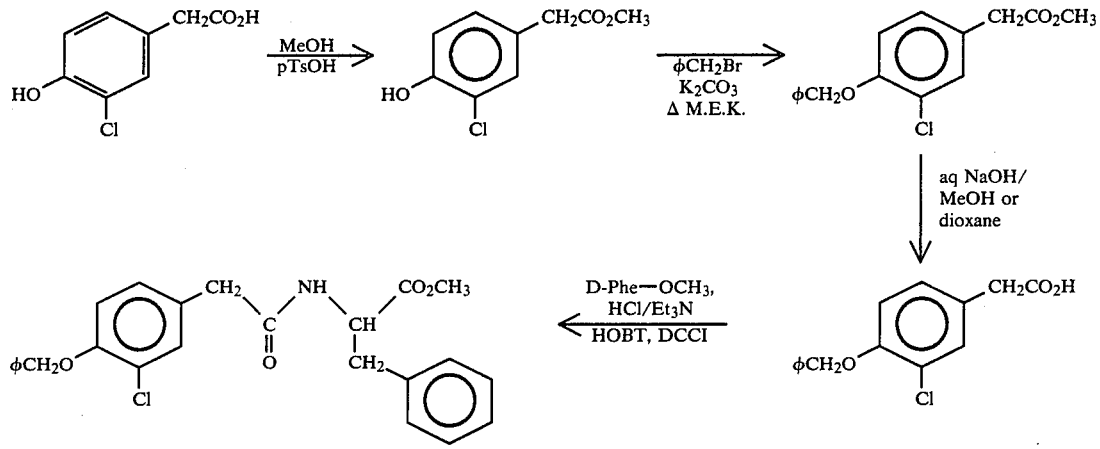

phase was acidified with 2N hydrochloric acid. The desired free acid was separated, was extracted into ethyl acetate, washed with water and dried over anhydrous magnesium sulfate. Filtration and evaporation afforded a pale yellow solid. This yellow solid was recrystallized from ethyl acetate/cyclohexane in the presence of charcoal to give white crystals of m.p. 121°–123° C. The crystals were found homogeneous when subjected to t.l.c. on a silica plate using a solvent system of 85:10:5 v/v of chloroform, methanol and acetic acid. A N.M.R. spectrum was consistent with the structure of 4-benzyloxy-3-chlorophenylacetic acid.

EXAMPLE 1A

Methyl 3-Chloro-4-Hydroxyphenylacetate

A mixture of 67 g (0.38 moles) of 3-chloro-4-hydroxyphenylacetic acid, 1.5 g of p-toluenesulfonic acid, and 250 ml of methanol was refluxed overnight, i.e., about 18 hours. The excess methanol was removed by vacuum to give a thick tawny oil. This oil was dissolved in ether, twice washed with water, and dried over anhydrous sodium sulphate. The ethereal solution was filtered, the ether removed and a tawny oil remained. Using as solvent 2.5% v/v methanol in chloroform and a silica gel matrix, thin-layer chromatography showed that the oil was essentially homogeneous, there being only a trace impurity present at the origin, which is believed to be unreacted acid. This oil was satisfactory for use as the starting material for forming the ether of Example 1B.

EXAMPLE 1B

Methyl 4-Benzyloxy-3-Chlorophenylacetate

A mixture of 8.7 g (43.4 mmoles) of methyl 3-chloro-4-hydroxyphenylacetate, 6.2 g (44.8 mmoles) of powdered anhydrous potassium carbonate, 7.6 g (44.6 mmoles) of benzyl bromide, and 25 ml of methyl ethyl ketone was refluxed for six hours.

After cooling, the reaction mixture was diluted with 200 ml of water, and thrice extracted with ether. The combined ethereal extracts were washed thrice with 10% w/v aqueous sodium carbonate solution, twice with water and dried over anhydrous magnesium sulphate. The drying agent was filtered off and the ether removed to give a somewhat discolored oil. T.l.c. showed this oil to be virtually pure and satisfactory for the subsequent saponification described in Example 1C.

EXAMPLE 1C

4-Benzyloxy-3-Chlorophenylacetic Acid

The entire product obtained in Example 1B was dissolved in 10 ml of methanol. To this solution was added a solution of 6 g of sodium hydroxide (150 mmoles) in 20 ml of water. The mixture was stirred for one hour at room temperature followed by stirring for one hour at 40° C. The solution was then diluted with 200 ml of water and washed three times with ether. The aqueous

EXAMPLE 1D

4-Benzyloxy-3-Chlorophenylacetyl-D-Phenylalanine Methyl Ester 0.85 g (5.5 mmoles) of 1-hydroxybenzotriazole hydrate was dissolved in 20 ml of tetrahydrofuran. To this solution was added 1.38 g (5 mmoles) of 4-benzyloxy-3-chlorophenylacetic acid. The mixture was stirred until a homogeneous solution was obtained. To this solution was added 20 ml of methylene chloride, and the resulting solution was chilled to 0°–5° C. in an ice-bath. A 2.5 ml (5 mmoles) solution of 2M dicyclohexylcarbodiimide in toluene was introduced and the mixture stirred for about five minutes at 0°–5° C. The cooling bath was removed and the mixture was stirred for twenty to thirty minutes at room temperature; during this period, crystals of dicyclohexylurea separated. The suspension was then chilled again to 0°–5° C. (First suspension)

Parallel in time for preparing the first suspension, a second suspension was prepared as follows. 1.62 g (7.5 mmoles) of D-phenylalanine methyl ester hydrochloride was suspended in 30 ml of methylene chloride. 0.91 ml (6.5 mmoles) of triethylamine was added, whereupon the bulk of the solid dissolved. This mixture was chilled to 0°–5° C. (Second suspension)

The first suspension was filtered through a sintered glass funnel to room dicyclohexylurea; this, in turn was washed with 15 ml of methylene chloride. The combined filtrate and washings were added to the chilled second suspension. The mixture was chilled for about thirty minutes and then stirred overnight at room temperature.

The next day, the solvent was evaporated off under reduced pressure to give a gummy solid. This solid was dissolved in about 20 ml chloroform and filtered to remove any residual dicyclohexylurea. The filtrate was evaporated and the residue taken up in ethyl acetate. The solution was washed successively with 0.5N aqueous citric acid soution three times, then with saturated aqueous sodium bicarbonate solution three times followed by twice washing with water. The washed organic solution was dried over anhydrous magnesium sulfate, filtered, and the solvent removed under reduced pressure. Trituration of the residue with petroleum ether afforded a crystalline solid. Recrystallization from 75% ethanol/25% water (v/v) in the presence of charcoal afforded 0.70 g white crystals having a mp 92°–94° C. The N.M.R. spectrum was consistent with the structure. The material was chromatographically homogeneous when subjected to thin layer chromotography on silica-gel plates using 2.5% v/v methanol in chloroform as the eluent.

Analyses: Calculated for: C, 68.56; H, 5.52; N, 3.22; found: C, 68.52; H, 5.55; N, 3.03

In like manner as above, using appropriate starting materials and reagents, the following compounds were prepared:

| Name of Compound | M.P.(°C.) |
| --- | --- |
| 4-Allyloxy-3-chlorophenylacetyl-DL-p-chlorophenylalanine | 99° |
| 4-Allyloxy-3-chlorophenylacetyl-N—benzylglycine ethyl ester | oil |
| 4-Allyloxy-3-chlorophenylacetyl-D-phenylalanine methyl ester | 82–84° |
| 3-Chloro-4-n-propyloxyphenylacetyl-D-phenylalanine methyl ester | 59–62° |
| N—[4-Allyloxy-3-chlorophenylacetyl]-L-phenylalaninol | 126–127° |
| 4-Benzyloxyphenylacetyl-D-phenylalanine methyl ester | 121–123° |
| 4-Benzyloxyphenylacetyl-L-phenylalanine methyl ester | 121–123° |
| N—benzyl, N—[2-hydroxyethyl]-3-chloro-4-allyloxyphenylacetamide; | 49° |
| N—[4-Allyloxy-3-chlorophenylacetyl]-S-hydroxy-L-phenylalaninol | 84° |
| N—[4-Allyloxy-3-chlorophenylacetyl]-1-amino-2-phenylpropane | 77° |
| 4-Allyloxy-3-chlorobenzoyl-L-phenylalanine methyl ester | 81–83° |
| 4-[2-Cyclohexenyloxy]-benzoyl-L-phenylalanine methyl ester | 111–113° |
| N—[4-Allyloxy-3-chlorophenylacetyl]-1-hydroxy-1-[4-hydroxyphenyl]-2-aminopropane | 120–122° |
| 4-Allyloxy-3,5-dichlorophenylacetyl-L-phenylalanine | 131–132° |
| 4-Allyloxy-3-chlorophenylacetyl-S—benzyl-L-cysteine methyl ester | 86–88° |
| 3-Chloro-4-propargyloxyphenylacetyl-D-phenylalanine methyl ester | 97–99° |
| 3-Chloro-4-methoxyphenylacetyl-D-phenylalanine methyl ester | 100–102° |
| 4-Allyloxy-3-chlorophenylacetyl-(+)-ephedrine | oil |
| N—[4-Allyloxy-3-chlorophenylacetyl]-N—methyl-2-hydroxy-2-phenylethylamine | oil |
| N—[4-Allyloxy-3-chlorophenylacetyl]-N—methyl-2-phenylethylamine | oil |
| N—benzyl, N—methyl-3-chloro-4-allyloxyphenylacetamide | oil |
| 3-Chloro-4-phenylethyloxyphenylacetyl-D-phenylalanine methyl ester | 106–108° |
| N—[4-Allyloxy-3-chlorophenylacetyl]-2-hydroxy-2-phenylethylamine | |
| N—[3-Chloro-4-phenylethyloxyphenylacetyl]-N—methyl-2-hydroxy-2-phenylethylamine | oil |
| 3-Chloro-4-isopropyloxyphenylacetyl-D-phenylalanine methyl ester | 84–86° |
| N—[3-Chloro-4-phenylethyloxyphenylacetyl]-N—methyl-2-phenylethylamine | oil |
| N—[4-Benzyloxy-3-chlorophenylacetyl]-N—methyl-2-phenylethylamine | oil |
| N—[3-Chloro-4-methoxyphenylacetyl]-N—methyl-2-phenylethylamine | oil |
| 4-Benzyloxy-3-fluorophenylacetyl-D-phenylalanine methyl ester | 114–116° |
| 4-Benzyloxy-3-chlorophenylacetyl-D-tryptophan methyl ester | 148–150° |
| 4-Benzyloxy-chlorophenylacetyl-D-phenylalanine | 121–123° |
| 3-Chloro-4-cyclopropylmethyloxyphenylacetyl-D-Phenylalanine methyl ester | 87–89° |
| 3-Chloro-4-[2-quinolinemethyloxy]phenylacetyl-D-phenylalanine methyl ester | 162–163° |
| 3-Chloro-4-phenylethyloxyphenylacetyl-N—methyl-D-phenylalanine methyl ester | oil |

As therapeutic agents, compounds of the present invention are characterized by anti-hypersensitivity, anti-inflammatory, anti-allergic and anti-asthma activity.

The therapeutic agents of this invention may be administered alone or in combination with pharmaceutically-acceptable carriers, the proportion of which is determined by the solubiity and chemical nature of the compound, chosen route of administration and standard pharmaceutical practice. For example, they may be administered orally in the form of tablets or capsules containing such excipients as starch, milk sugar, certain types of clay and so forth. They may be administered orally in the form of solutions which may contain coloring and flavoring agents or they may be injected parenterally, that is, intramuscularly, intravenously or subcutaneously. For parenteral administration, they may be used in the form of a sterile solution containing other solutes, for example, enough saline or glucose to make the solution isotonic.

The physician will determine the dosage of the present therapeutic agents which will be most suitable and it will vary with the form of administration and the particular patient under treatment. He will generally wish to initiate treatment with small dosages substantially less than the optimum dose of the compound and increase the dosage by small increments until the optimum effect under the circumstances is reached. It will generally be found that when the composition is administered orally, larger quantities of the active agent will be required to produce the same effect as a smaller quantity given parenterally. The compounds are useful in the same manner as other anti-hypersensitivity agents and the dosage level is of the same order of magnitude as is generally employed with these other therapeutic agents. The therapeutic dosage will generally be from 10 to 75 milligrams per day and higher although it may be administered in several different dosage units. Tablets containing from 10 to 250 mg of active agent are particularly useful.

Compounds according to the invention have been subjected to pharmacological testing in order to assess their anti-inflammatory, anti-allergy, or anti-asthma activity.

First, a brief explanation of the physiological mechanism believed to take place which is then beneficially affected by the compounds of the present invention follows.

The Lipoxygenase Cascade and its Role in Disease

Arachidonic acid (AA) is released from phospholipids upon stimulation of specific membrane receptors (Crews, F. T., Mortea, J., Herata, F., Axelrod, J., Seraganian, R. P.: Phospholipid Methylation Affects Immunogloblin E. Mediated Histamine and Arachidonic Acid Release in Rat Leukemic Basophils. Biochemical and Biophysical Research Communications 93 42–46 (1980)). IgE-mediated cross-linking of IgE-receptors in the mast cell, for example, results in the enzyme-catalyzed release of AA.

The oxidative metabolism of AA has been shown recently to occur by two main pathways (a. Hamberg, M., Samuelsson, B.: Prostaglandin Endoperoxides, Novel Transformation of Arachidonic Acid in Human Platelets. Proc. Nat. Acad. Sci. 71 3400–3404 (1974); b. Blackwell, G. J., Duncombe, W. G., Flower, R. I., Parsons, M. F., Vane, J. R.: The Distribution and Metabolism of Arachidonic Acid in Rabbit Platelets During Aggregation and its Modification by Drugs. J. Pharmacology 59 353–366 (1977)). The first is via a membrane bound cyclooxygenase, which converts AA into an endoperoxide, which is transformed into prostaglandins, prostacyclin, or thromboxanes. The second pathway, elucidated by Samuelsson and others (Borgeat, P., Samuelsson, B.: Arachidonic Acid Metabolism in Polymorphonuclear Leukocytes: Unstable Intermediate in Formation of Dihydroxy Acid. Proc. Nat. Acad. Sci. 76 3213–3217 (1979)), is initiated by a lipoxygenase which attacks cis, cis-1, 4-double bonds, oxidizing AA into hydroperoxyeicosatetraenoic acids (HPETEs) and their stable products hydroxyeicosatetraenoic acids (HETEs).

Lipoxygenases are classified according to the position in the AA which is oxygenated. Platelets metabolise AA to 12-HETE, while polymorphonuclear leukocytes contain 5- and 15-lipoxygenases. It has been shown that 12-HETE and 5,12 -diHETE are chemotactic for human neutrophils and eosinophils, and may augment the inflammation process (a. Goetzel, E. J., Weller, P. F., Sun, F. F.: Regulation of Human Eosinophil Function by Endogenous Monohydroxy-Eicosatetrainoic Acids. J. Immunology 124 926–933 (1980), b. Turner, S., Tainer, J., Lynn, W.: Biogenesis of Chemotactic Molecules by the Arachidonic Lipoxygenase System of Platelets. Nature 257 630–681 (1975)). Still others report on the involvement of leukotrienes and other lipoxygenase products in the pathogenesis of psoriasis (Voorhees, J. J., Leukotrienes and other Lipoxygenase Products in the Pathogeneis and Therapy of Psoriasis and other Dermatoses. Arch. Dermatol. 119 541–547 (1983)). Oxidation of AA at the 5-position produces 5-HPETE, which has been shown to be a precursor of SRS-A, a combination of $LTC_4$ and $LTD_4$. Upon antigenic challenge of sensitized mast cells, SRS-A is synthesized and released along with histamine and other mediators of anaphylaxis. SRS is also produced by monocytes and neutrophils treated with calcium ionophore (Borgeat, P., Samuelsson, B.: Arachidonic Acid Metabolism in Polymorphonuclear Leukocytes: Effects of Ionophore A23187. Proc. Nat. Acad. Sci. 76 2148–2152 (1979)). The SRS family of molecules (leukotrienes C and D) have been shown to be potent bronchoconstrictors (Dahler, S., Hedqvist, P., Hammarstrom, S., Samuelsson, B.: Leukotrienes are Potent Constrictors of Human Bronchi. Nature 288 484–486 (1980)), and are proposed to play an important role in asthma (see Review by M. K. Bach, Prospects for Inhibition of Leukotriene Synthesis. Biochem. Pharmacol. 33 (4) 515–521 (1984)).

Other pathophysiologic roles for products of the 5-lipoxygenase pathway are in chronic aspects of acute respiratory distress syndrom (ARDS), as well as in inflamed bowel disease (Review by M. K. Bach, Prospects for Inhibition of Leukotriene Synthesis. Biochem. Pharmacol. 33 (4) 515–521 (1984)).

Thus, reports and hypothesis in the medical literature support a role for lipoxygenase products in general inflammatory disease states (such as rheumatoid arthritis), certain dermatologic conditions (e.g. psoriasis) and bronchopulmonary disease states such as asthma and ARDS.

Protocol for the Biosynthesis of 5-HETE (5(S)-Hydroxyeicosatetraenoic Acid) by Human Polymorphonuclear Leukocytes In Vitro (A) Isolation of Human Neutrophils Freshly drawn venous blood from healthy human volunteers is mixed with 2 mM ethylenediamine tetra-acetic acid, and is sedimented at $1 \times g$ over 6% dextran-saline. The leukocyte layer is aspirated, and the cells are concentrated by centrifugation and are layered over stacked Percoll ® solutions, having densities of 1.072, 1.082 and 1.100, respectively. PMNs are isolated at the interface between the two densest layers after centrifugation at $400 \times g$. Contaminating red blood cells are lysed by a short treatment of 0.16M ammonium chloride.

(B) The Assay

A suspension of human neutrophils in buffer is incubated for 3 minutes at 30° C. with ($^{14}$C)-arachidonic acid (AA) and calcium ionophore A23187. Citric Acid (2M)/NDGA*(10 mM) is used to quench the reaction. Following the addition of a trace amount of ($^3$H)-5-HETE together with an excess of unlabeled 5-HETE to each tube, the mixture is extracted with chloroform/methanol. The organic layer is washed with dilute hydrochloric acid and the total volume is transferred to glass tubes and dried in vacuo. The residue is dissolved in a small volume of chloroform and is spotted on silica gel TLC sheets, which are developed with an ethyl acetate/iso-octane/water/acetic acid solvent system (11/5/10/1 v/v). The 5-HETE spots are visualized under UV light, cut out and placed in scintillation vials for quantitation of radioactivity. After adjusting for the extraction efficiency, the amount (pmole) of ($^{14}$C)-5-HETE in each of the tubes is calculated. The net pmoles of 5-HETE are obtained by subtracting the pmole of 5-HETE in the tubes containing buffer alone (blank) from the pmoles of 5-HETE in the tubes containing buffer and cells (control). The ability of the test compound to modulate the activity of this enzyme is determined by a decrease or increase in the net amount of 5-HETE produced. This assay is a modification of that described by Bach and Brashler for rat peritoneal cells: Bach, M., Brashler, J.: Ionophore A23187-Induced Production of SRS-A by Rat Peritoneal Cells In Vitro: Evidence for Production by Mononuclear Cells. J. Immunol. 120 998–1005 (1978).

*NDGA-nordihydroguaiaretic acid

Protocol for the Biosynthesis of 5-HETE by Rat Polymorphonuclear Leukocytes In Vitro A suspension of rat neutrophils in buffer is incubated for 3 minutes at 30° C. with [$^{14}$C]-arachidonic acid (AA) and calcium ionophore A23187. Citric Acid (2M) NDGA (10 mM) is used to quench the reaction. Following the addition of a trace amount of ($^3$H)-5-HETE together with an excess of unlabeled 5-HETE to each tube, the mixture is extracted with chloroform/methanol. The organic layer is washed with dilute acid and an aliquot is transferred to glass tubes and dried. The residue is dissolved in a small volume of chloroform and an aliquot is spotted on silica gel TLC sheets, which are developed with an ethyl acetate/isoctane/water/acetic acid solvent system. The 5-HETE spots are visualized under UV light, cut out and placed in scintillation vials for counting. After adjusting for the extraction efficiency, the amount (pmole) of [$^{14}$C]-5-HETE in each of the tubes is quantitated. The net pmoles of 5-HETE are obtained by subtracting the pmoles of 5-HETE in the tubes containing buffer alone (blank) from the pmoles of 5-HETE in the tubes containing buffer and cells (control). The ability of the test compounds to modulate the activity of this enzyme is determined by a decrease or increase in the net amount of 5-HETE produced.

Protocol for Antagonism of Leukotrines C-4 Binding

Peripheral strips of guinea pig lungs are prepared and hung in tissue baths according to the procedure described by Drazen et al. (Proc. Nat'l. Acad. Sci., U.S.A. 77, 4354–4358, 1980). Male guinea pigs (Charles River, 250–400 g) are sacrificed by cervical dislocation and their lungs rapidly removed. The individual lobes are dissected free and rinsed in Assay Buffer (118 mM NaCl, 5.4 mM KCl, 2.5 mM $CaCl_2$, 25 mM $NaH_2CO_3$, 1 mM $MgSO_4$, 1 mM $NaH_2PO_4$, 11 mM glucose) which is continuously aerated with 95% oxygen/5% carbon dioxide. After the lobes are extensively rinsed, a strip of lung tissue, approximately 2 mm thick and 5–8 cm long, is cut off the sharpest and most peripheral portion of each lobe. The peripheral edge is cut almost completely around the outside of the lobe so that a U-shaped strip is obtained. These strips are rinsed in Assay Buffer and then connected with surgical silk thread to the support rods of the water jacketed tissue baths (10 ml chambers). The other ends of the strips are connected to Gould UC3 pressure transducers which had been previously calibrated. The tissue baths are aerated with 95% oxygen/5% carbon dioxide and maintained at 37° C. The tension on these strips are adjusted to 500 mg. The tissues are initially washed with fresh buffer every 5–10 minutes for about 30 minutes and thereafter washed with fresh assay buffer at least every 20 minutes.

After the tissue had been repeatedly washed and allowed to equilibrate in the tissue baths, they are challenged with 1 μM histamine to standardize the contractions for each tissue.

Responses of each tissue to a predetermined concentration (usually 0.2 nM) of leukotriene $C_4$ are then obtained. Compounds are then tested for their ability to antagonize to leukotriene $C_4$ immediately upon challenge.

Table I contains illustrative results for all tests.

All compounds are first screened using an effective concentration of 10 μM or 30 μM as indicated in the Table.

If the percentage of inhibition exceeds 50%, the compounds are then evaluated in terms of response over a range of concentrations. From a plot of response against concentration, the $I_{50}$ value is obtained. The $I_{50}$ value is the concentration at which 50% inhibition is observed.

TABLE I

| | Inhibition of Lipoxygenase | | | | |
|---|---|---|---|---|---|
| | INHIBITION OF RAT 5-LIPOXYGENASE % Inhibition | | INHIBITION OF HUMAN 5 LIPOXYGENASE % Inhibition | | ANTAGONISM OF $LTC_4$ BINDING |
| Name | at 10 μM | $I_{50}$ (μM) | at 30 μM | $I_{50}$ (μM) | $I_{50}$ (μM) |
| 4-Allyloxy-3-chlorophenylacetyl-L-phenylalanine methyl ester | 27 | | | | 5 |
| 4-Allyloxy-3-chlorophenylacetyl-DL-p-chlorophenylalanine methyl ester | 25 | | | | 9 |
| 4-Allyloxy-3-chlorophenylacetyl-N—benzylglycine ethyl ester | | 8 | | | 20 |
| 4-Allyloxy-3-chlorophenylacetyl-D-phenylalanine methyl ester | | 0.7 | | | 9 |
| 3-Chloro-4-n-propyloxyphenylacetyl-D-phenylalanine methyl ester | | 0.8 | | 6 | 9 |
| N—[4-Allyloxy-3-chlorophenylacetyl]-L-phenylalaninol | 33 | | | | 3 |
| 4-Benzyloxyphenylacetyl-L-phenylalanine methyl ester | 29 | | | | 5 |
| N—benzyl, N—[2-hydroxyethyl]-3-chloro-4-allyloxyphenylacetamide | 41 | | | | |
| N—[4-Allyloxy-3-chlorophenylacetyl]-3S-hydroxy-L-phenylalaninol | 36 | | | | |
| N—[4-Allyloxy-3-chlorophenylacetyl]-1-amino-2-phenylpropane | 18 | | | | 2.5 |
| 4-Allyloxy-3-chlorobenzoyl-L-phenylalanine methyl ester | 34 | | | | 15 |
| 4-[2-Cyclohexenyloxy]-benzoyl-L-phenylalanine methyl ester | 33 | | | | |
| 4-Benzyloxy-3-chlorophenylacetyl-D-phenylalanine methyl ester | | 0.25 | | 0.6 | |
| 3-Chloro-4-propargyloxyphenylacetyl-D-phenylalanine methyl ester | | 0.5 | | 1.5 | 12 |
| 3-Chloro-4-methoxyphenylacetyl-D-phenylalanine methyl ester | | 3.8 | | | |
| 4-Allyloxy-3-chlorophenylacetyl-(+)-ephedrine | 15 | | | | |
| 4-Allyloxy-3-chlorophenylacetyl-(−)-ephedrine | 30 | | | | |
| N—[4-Allyloxy-3-chlorophenylacetyl]-N—methyl-2-hydroxy-2-phenylethylamine | | 1.8 | | | 18 |
| N—[4-Alloyoxy-3-chlorophenylacetyl]-N—methyl-2-phenylethylamine | | 2.4 | | 2 | 3 |

TABLE I-continued

| | Inhibition of Lipoxygenase | | | | ANTAGONISM OF LTC$_4$ BINDING |
|---|---|---|---|---|---|
| | INHIBITION OF RAT 5-LIPOXYGENASE % Inhibition | | INHIBITION OF HUMAN 5 LIPOXYGENASE % Inhibition | | |
| Name | at 10 μM | I$_{50}$ (μM) | at 30 μM | I$_{50}$ (μM) | I$_{50}$ (μM) |
| N—benzyl, N—methyl-3-chloro-4-allyloxy-phenylacetamide | | 20 | | | |
| 3-Chloro-4-phenylethyloxyphenylacetyl-D-phenylalanine methyl ester | | 0.7 | | 7 | |
| N—[4-Allyloxy-3-chlorophenylacetyl]-2-hydroxy-2-phenylethylamine | | 20 | | | |
| N—[3-Chloro-4-phenylethyloxyphenylacetyl]-N—methyl-2-hydroxy-2-phenyl-ethyl-amine | | 3 | | 10 | 5 |
| 3-Chloro-4-isopropyloxyphenylacetyl-D-phenylalanine methyl ester | | 2 | 95 | | |
| N—[3-Chloro-4-phenylethyloxyphenylacetyl]-N—methyl-2-phenylethylamine | | 2.2 | | 8 | |
| N—[4-Benzyloxy-3-chlorophenylacetyl]-N—methyl-2-phenylethylamine | | 4.2 | | 2 | |
| N—[3-Chloro-4-methoxyphenylacetyl]-N—methyl-2-phenylethylamine | 33 | | | | |
| 4-Benzyloxy-3-chlorophenylacetyl-D-tryptophan methyl ester | | 5.4 | | 14 | |
| 4-Benzyloxy-3-chlorophenylacetyl-D-phenylalanine | 40 | | | | |
| 3-Chloro-4-cyclopropylmethyloxyphenylacetyl-D-phenylalanine methyl ester | | 1 | | 50 | |
| 1-Chloro-4-[2-quinolinemethyloxy]-phenylacetyl-D-phenylalanine methyl ester | 50 | | | | |
| 3-Chloro-4-phenylethyloxyphenylacetyl-N—methyl-D-phenylalanine methyl ester | | 5 | 28 | | |

What is claimed is:

1. A compound of the molecular structure represented by the formula

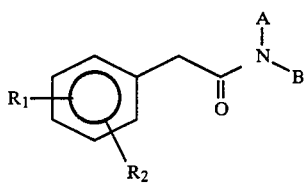

and pharmaceutically acceptable salts thereof, wherein
R$_1$ is H, lower alkyl, aryl-lower alkoxy, lower alkenoxy, lower alkynoxy, or halogen;
R$_2$ is lower alkoxy, aryl-lower alkoxy, lower alkenoxy, or lower alkynoxy with the proviso that when R$_1$ is halogen, R$_2$ cannot be lower alkoxy or lower alkenoxy, and wherein aryl in aryl-lower alkoxy is phenyl or napthyl;
A is H, or lower alkyl; and
B is

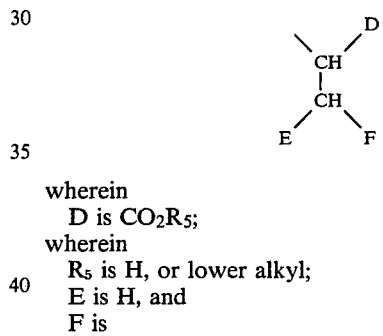

wherein
D is CO$_2$R$_5$;
wherein
R$_5$ is H, or lower alkyl;
E is H, and
F is

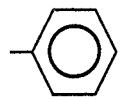

2. The compound of N-[3-chloro-4-propargyloxy-phenylacetyl]-D-phenylalanine methyl ester.

3. The compound of N-[4-benzyloxy-3-chloro-phenylacetyl]-D-phenylalanine methyl ester.

4. The compound of N-[3-chloro-4-phenylethyloxy-phenylacetyl]-N-methyl-D-phenylalanine methyl ester.

5. The compound of N-[3-chloro-4-phenylethyloxy-phenylacetyl]-D-phenylalanine methyl ester.

6. A pharmaceutical composition for the treatment of allergic conditions in a mammal comprising a compound of claim 1 in a pharmaceutically acceptable carrier.

7. A pharmaceutical composition for the treatment of inflammatory conditions in a mammal comprising a compound of claim 1 in a pharmaceutically acceptable carrier.

* * * * *